US00PP25751P3

(12) United States Plant Patent
Schoone

(10) Patent No.: US PP25,751 P3
(45) Date of Patent: Jul. 28, 2015

(54) ***PHALAENOPSIS* ORCHID PLANT NAMED 'GOODHOPE'**

(50) Latin Name: *Phalaenopsis hybrida*
Varietal Denomination: Goodhope

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 120 days.

(21) Appl. No.: 13/986,273

(22) Filed: Apr. 18, 2013

(65) Prior Publication Data

US 2013/0291246 P1 Oct. 31, 2013

Related U.S. Application Data

(60) Provisional application No. 61/638,141, filed on Apr. 25, 2012.

(30) Foreign Application Priority Data

Apr. 26, 2012 (NL) ..... PBR OPS899

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
CPC ..... A01H 5/02; A01H 5/00
See application file for complete search history.

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Goodhope' particularly characterized by flowers which are red/purple with white edges and some white marks and a little yellow/orange in the labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Goodhope'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Goodhope'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Goodhope' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Goodhope' originated from a cross made by the inventor in 1999 in Strengweg, Heemskerk, The Netherlands. The female or seed parent is the *Phalaenopsis* cultivar designated 'King Shiang's Rose', unpatented. The male or pollen parent is the *Phalaenopsis* cultivar designated 'Red Charm', unpatented. The new *Phalaenopsis* 'Goodhope' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture (mericloning) was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Goodhope', which in combination distinguish this *Phalaenopsis* as a new and distinct cultivar:

1. flowers which are red/purple with white edges and some white marks and a little yellow/orange in the labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Goodhope', the female parent 'King Shiang's Rose' has dark pink/red flowers and the male parent 'Red Charm' has red colored flowers, whereas the flowers of 'Goodhope' are red/purple with white edges and some white marks.

Presently, a commercial cultivar to which 'Goodhope' can be meaningfully compared is 'Elegant Debora' (unpatented). The flowers of 'Goodhope' are about 95 mm in size and have white marks on the petals and sepals. The flowers of 'Elegant Debora' are about 75 mm in size and have white edges. Both flowers are red/purple, but at 'Goodhope' the purple dominates and at 'Elegant Debora' the red dominates.

BRIEF DESCRIPTION OF THE PHOTOGRAPHS

The accompanying photographs illustrate the overall appearance of the new *Phalaenopsis* 'Goodhope' showing the colors as true as is reasonably possible with colored reproductions of this type. Colors in the photographs may differ slightly from the color values cited in the detailed botanical description, which accurately describe the color of 'Goodhope'.

DETAILED BOTANICAL DESCRIPTION

Figure 1:
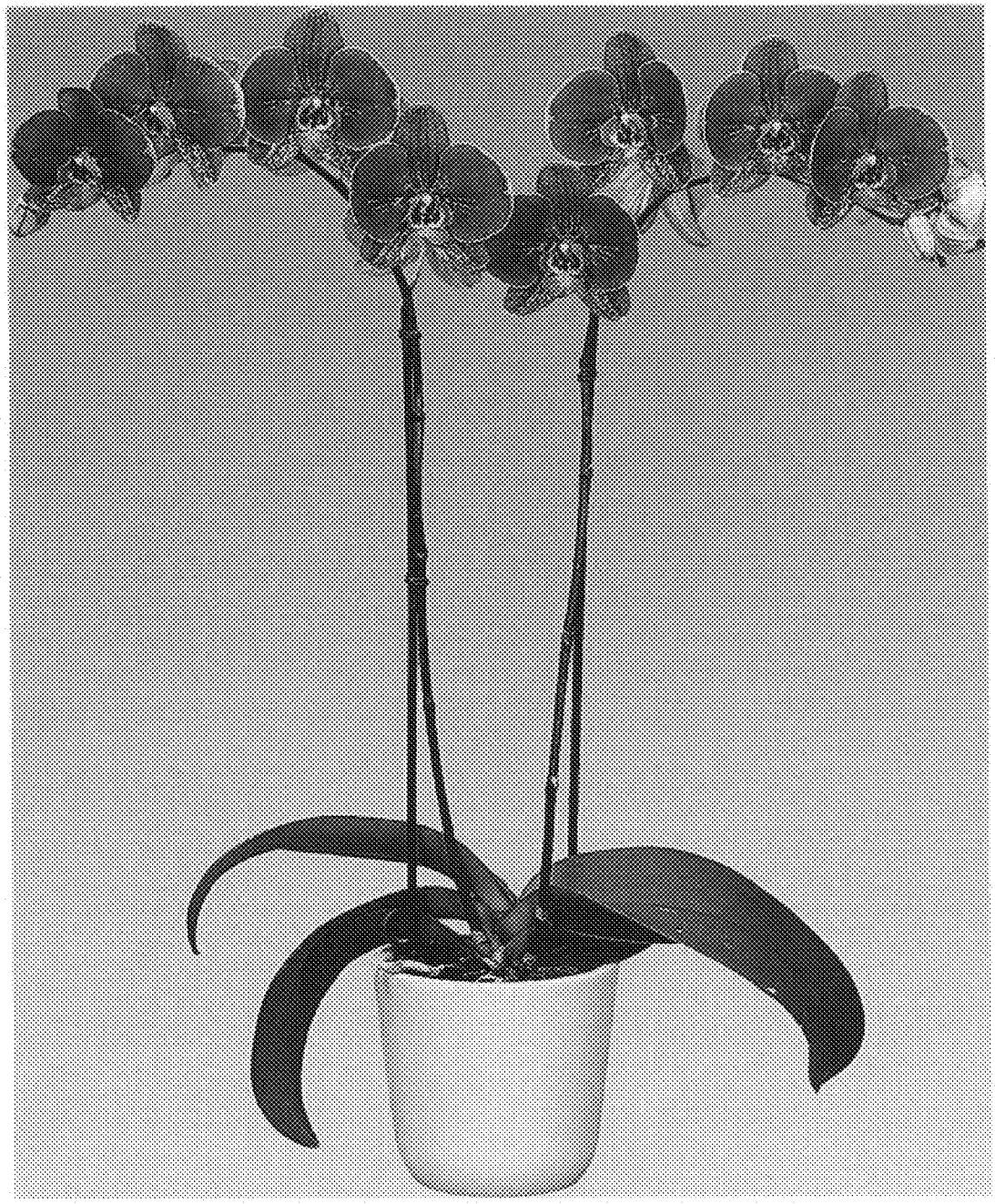
FIG. 1 shows a side view perspective of a typical flowering plant of 'Goodhope' in a 12 cm pot, at 16 months of age.

The new *Phalaenopsis* cultivar 'Goodhope' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Goodhope' as grown in a greenhouse in Strengweg, Heemskerk, The Netherlands, under conditions which closely approximate those generally used in commercial practice. Initially, the ideal temperature to grow plants of 'Goodhope' is 27° C. during the day and at night. Then, during the flowering phase of 'Goodhope', the ideal growing temperature is 20-22° C. during the day and 18° C. at night. Light levels for growing 'Goodhope' are a minimum of 5,000 lux and a maximum of 10,000 lux. A balanced fertilizer with level of 200 ppm N, 87 ppm P, 168 ppm K is applied. Duration of growth of 'Goodhope' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Goodhope' plants described is 12 months after potting.

Classification:

*Botanical.—Phalaenopsis hybrida.*

Parentage:

*Female or seed parent.—Phalaenopsis* cultivar designated 'King Shiang's Rose', unpatented.

*Male or pollen parent.—Phalaenopsis* cultivar designated 'Red Charm', unpatented.

Propagation:

*Type*.—Tissue culture.

*Rooting habit and description*.—Fleshy; approximately 3 mm-7 mm wide and green in color (RHS 191B); freely branching. It takes 12 weeks for plants growing in tissue culture to initiate roots.

Plant:

*Size at maturity*.—Height: about 62 cm. Spread: about 55 cm.

*Growth habit*.—Standard; green leaves and a relatively normal raceme.

*Vigor*.—Moderate.

*Crop time*.—Following asexual propagation, at about 26 weeks 2 leaves appear; at about 30 weeks 3-4 leaves appear; after a cold treatment of about 4-8 weeks at a temperature of about 19° C. about 1-2 racemes with flowers appear.

Foliage:

*Quantity per plant*.—About 6 to 8 leaves are produced before flowering.

*Arrangement and attachment*.—Half up/horizontal and on two sides.

*Overall shape of leaf*.—Oval, the tip blunt and asymmetric.

*Texture* (*upper & underside*).—Smooth and leathery.

*Pubescence*.—None.

*Mature leaf length*.—About 19 to 25 cm.

*Mature leaf width*.—About 7 cm.

*Mature leaf thickness*.—About 1.5 mm.

*Mature leaf color*.—Upper side: green (RHS N137A). Under side: green (RHS 137A).

*Leaf base*.—Acute.

*Margin*.—Entire.

*Venation*.—Pattern: parallel. Color of midvein: upper side: green (RHS N137A). under side: purple (RHS 137C).

Inflorescence description:

*Appearance*.—Upright to slightly pendant, racemose inflorescence with bilaterally symmetrical flowers that open in succession beginning with the lowermost flower.

*Buds*.—Height (from base to tip): about 15 mm. Diameter (at midpoint): about 9 mm. Shape: egg-shaped. Color: yellow/green (RHS 146B) and red/purple (RHS 71A).

Raceme: Quantity per plant: about 1 to 2. Number of flowers per raceme: about 7 to 12. Length: about 45 to 55 cm.

*Peduncle*.—Diameter: about 4 mm. Strength: strong. Aspect: upright. Texture: glabrous and smooth. Color: grey/brown (RHS N199A) with grey/green spots (RHS 146A).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
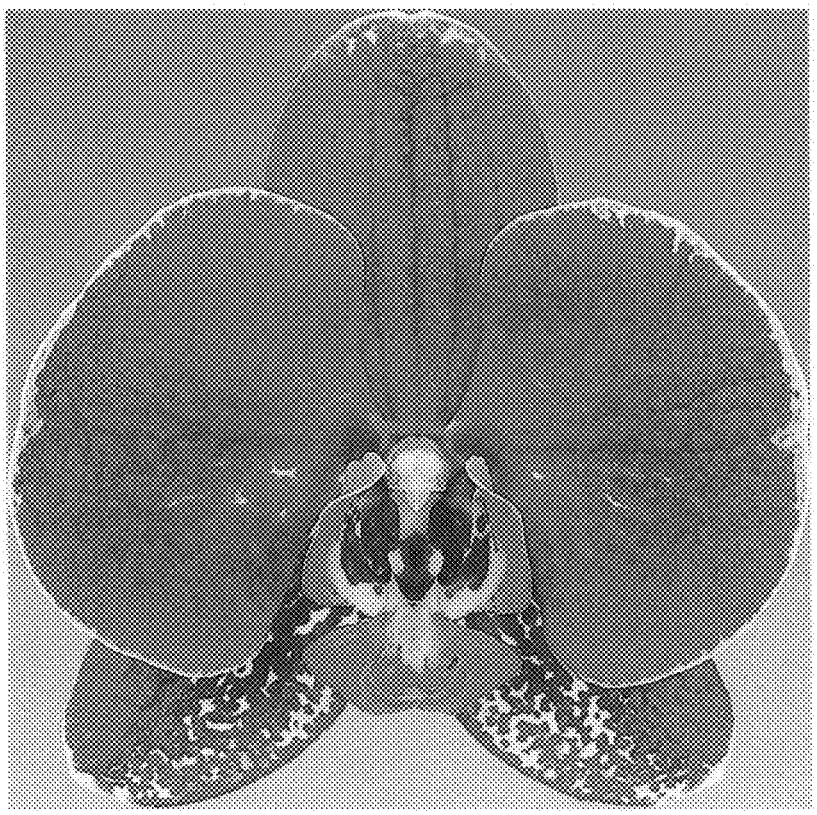
FIG. 2 shows a close-up view of a typical flower of 'Goodhope'.
Figure 3:
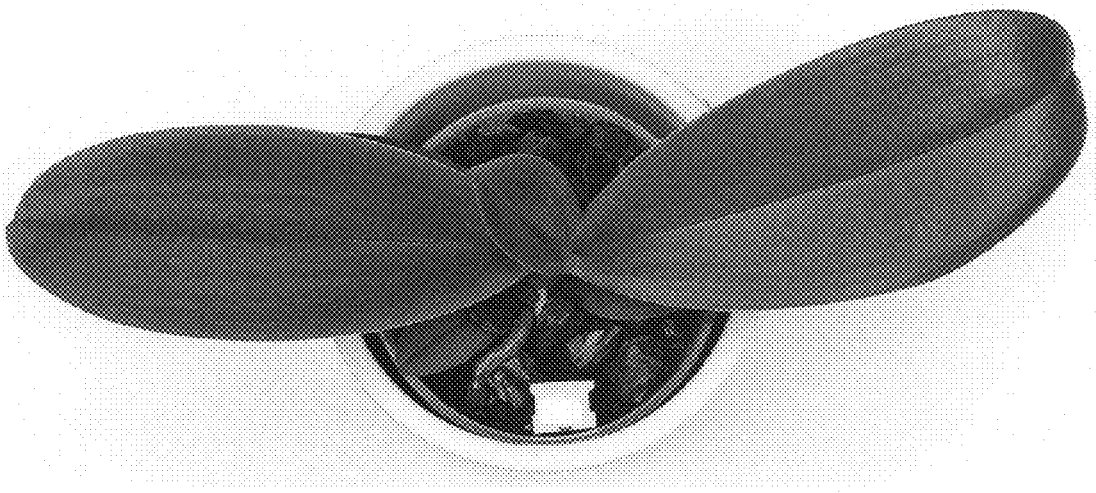
FIG. 3 shows a close-up view of the typical leaves of 'Goodhope'.

*Flower*.—Rate of opening: Flowers fully opened about 2 to 3 days after petal and sepal separation. Orientation at opening: slanted upward and outward. Shape: typical shape of *Phalaenopsis* orchid; see FIG. 2. Size: Height: about 90 mm. Diameter: about 95 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and a labellum. 2 lateral petals: Overall shape: broadly ovate and weakly cupped. Apex: oval. Margin: entire and weakly undulate. Base: broadly ovate. Length: about 50 mm. Width: about 45 mm. Texture: Upper surface: smooth and satiny. Under surface: smooth and satiny. Color (when fully opened): upper side: Main color is red/purple (RHS 71A) which runs out into red/purple (RHS 72A) and purple (RHS 77D). Edges and some marks are white (RHS NN155B). Under side: white (RHS NN155C) and purple (RHS 76A). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is rhombic with a bump and a rib on it. Margin: entire and weakly undulate. Apex: oval. Length midlobe: about 25 mm. Width (not flattened) midlobe: about 20 mm. Length lateral lobe: about 20 mm. Width (not flattened) lateral lobe: about 15 mm. Depth of tube created by lateral lobes of labellum: about 10 mm. Texture: Upper and under surface: smooth and satiny. Color (when fully opened): Midlobe: upper surface: At the base yellow (RHS 14C) which runs out into white (RHS 155B). Upper edge a small purple line and some spots (RHS 71A) From halfway it turns purple (RHS N78A). Under side: Edges are red/purple (RHS 71A) with some red/purple spots (RHS 59A). In the center some yellow (RHS 8B). Further mainly white (RHS 155B) and close to the cirrhi purple (RHS 71A). Lateral lobes: upper surface: From base white (RHS NN155B) and a red/purple mark and some spots (RHS 59A). On the upper edge purple (RHS 72B) and a little white (RHS N155C). Lower edge is red/purple (RHS 59A) with some yellow (RHS 8B). Under side: Upper edge is white (RHS 155C), lower edge red/purple (RHS 59A). From base white (RHS NN155C) which flows over in purple (RHS 72A). At the lower edge also some yellow (RHS 8A). Cirrhi: about 8 mm. color: red/purple (RHS 72A). Pestle (Callosities): Length: about 7 mm. Width (not flattened): about 5 mm. Color: sides yellow/white (RHS 158C) with a purple mark (RHS 77C). Top is yellow (RHS 8A) and inside and front is red/purple (RHS 59A).

*Sepals*.—Arrangement: Outer whorl comprises 3 sepals: one dorsal and two lateral sepals. Overall shape: elliptical and weakly cupped. Margin: entire and weakly undulate. Length: about 41 mm. Width: about 30 mm. Apex: dorsal: oval with notch; lateral: oval and little pointy. Texture: Upper and under surface: smooth and satiny. Color (when fully opened): upper surface: Dorsal: At the base purple (RHS N79C) then red/purple (RHS 72A) which runs into red/purple (RHS 71A). At the top some white (RHS NN155C). Lateral: At the base purple (RHS N79A) which runs into RHS N78A. There are some white marks (RHS NN155B). Underside: white (RHS NN155B) with purple (RHS 79A).

*Pedicel*.—Length: about 40 mm. Diameter: about 3 mm. Texture: glabrous and smooth. Color: white (RHS N155B) with some purple (RHS N80A), then yellow/green (RHS 145A) and ends in purple (RHS N79A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 7 mm. Diameter: about 5 mm. Color: purple (RHS N78A and RHS N78C) and some white (RHS NN155B).

*Pollinia*.—Quantity: two. Diameter: about 2 mm. Color: yellow/orange (RHS 23A).

*Ovary*.—Length: about 3 mm. Diameter: about 5 mm. Color: white (RHS 155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Goodhope', as illustrated and described herein.

* * * * *